US00PP17732P2

(12) United States Plant Patent

Parthasarathy et al.

(10) Patent No.: US PP17,732 P2
(45) Date of Patent: May 15, 2007

(54) *ANTHURIUM* PLANT NAMED 'RED SENSATION'

(50) Latin Name: *Anthurium hybrida*
Varietal Denomination: Red Sensation

(76) Inventors: Gopalaswamy Parthasarathy, 237/46, 'Srinivasa', Fifth Main Road, Chamrajpet, Bangalore 560018 (IN); Parthasarathy Mukundan, 127/46, 'Srinivasa', Fifth Main Road, Chamrajpet, Bangalore 560018 (IN)

( * ) Notice: Subject to any disclaimer, the term of this patent is extended or adjusted under 35 U.S.C. 154(b) by 0 days.

(21) Appl. No.: 11/264,771

(22) Filed: Nov. 1, 2005

(51) Int. Cl.
*A01H 5/00* (2006.01)

(52) U.S. Cl. ..... Plt./365
(58) Field of Classification Search ..... Plt./365
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Anthurium* plant named 'Red Sensation', characterized by its upright and outwardly arching plant form; freely clumping growth habit; medium to dark green-colored leaves; red-colored spathes with pale yellow to red-colored spadices that are positioned above and beyond the foliage on strong and erect scapes; freely flowering habit; and good inflorescence longevity.

1 Drawing Sheet

Botanical designation: *Anthurium hybrida.*
Cultivar denomination: 'Red Sensation'.

BACKGROUND OF THE INVENTION

The present Invention relates to a new and distinct cultivar of *Anthurium* plant, botanically known as *Anthurium hybrida* and hereinafter referred to by the name 'Red Sensation'.

The new *Anthurium* is the result of a planned breeding program conducted by the Inventors in Chamrajpet, Bangalore, India. The objective of the breeding program is to create new vigorous *Anthurium* cultivars with compact and dense plant habit, unique leaf coloration, interesting leaf shapes, resistance to pathogens and pests common to *Anthuriums* and tolerance to low temperatures.

The new *Anthurium* originated from a cross-pollination made by the Inventors on Jan. 12, 1995 of the *Anthurium andreanum* cultivar Chilli Red, not patented, as the female, or seed, parent with the *Anthurium hybrida* cultivar Lady Jane, not patented, as the male, or pollen, parent. The new *Anthurium* was discovered and selected by the Inventors as a single plant within the progeny of the stated cross-pollination in a controlled environment in Chamrajpet, Bangalore, India.

Asexual propagation of the new cultivar by cuttings since July, 1996 in a controlled environment in Chamrajpet, Bangalore, India, has shown that the unique features of this new *Anthurium* are stable and reproduced true to type in successive generations.

SUMMARY OF THE INVENTION

The following traits have been repeatedly observed and are determined to be the unique characteristics of 'Red Sensation'. These characteristics in combination distinguish 'Red Sensation' as a new and distinct cultivar of *Anthurium:*

1. Upright and outwardly arching plant form.
2. Freely clumping growth habit.
3. Medium to dark green-colored leaves.

4. Red-colored spathes with pale yellow to red-colored spadices that are positioned above and beyond the foliage on strong and erect scapes.
5. Freely flowering habit.
6. Good inflorescence longevity.

In side-by-side comparisons conducted by the Inventors in Chamrajpet, Bangalore, India, plants of the new *Anthurium* differed from plants of the female parent, the cultivar Chilli Red, in the following characteristics:

1. Leaves of plants of the new *Anthurium* were shorter, not as cordate and lighter green in color than leaves of plants of the cultivar Chilli Red.
2. Plants of the new *Anthurium* had smaller spathes than plants of the cultivar Chilli Red.

In side-by-side comparisons conducted by the Inventors in Chamrajpet, Bangalore, India, plants of the new *Anthurium* differed from plants of the male parent, the cultivar Lady Jane, in the following characteristics:

1. Leaves of plants of the new *Anthurium* were more cordate and lighter green in color than leaves of plants of the cultivar Chilli Red.
2. Plants of the new *Anthurium* had larger spathes than plants of the cultivar Chilli Red.

Plants of the new *Anthurium* can be compared to plants of the cultivar Red King, disclosed in U.S. Plant Pat. No. 13,381. In side-by-side comparisons conducted in northern Texas, plants of the new *Anthurium* differed from plants of the *Anthurium* cultivar Red King in the following characteristics:

1. Plants of the new *Anthurium* were smaller than plants of the cultivar Red King.
2. Leaves of plants of the new *Anthurium* were smaller and lighter green in color than leaves of plants of the cultivar Red King.
3. Plants of the new *Anthurium* had smaller spathes and shorter spadices than plants of the cultivar Red King.

BRIEF DESCRIPTION OF THE PHOTOGRAPH

The accompanying colored photograph illustrates the overall appearance of the new *Anthurium,* showing the colors as true as it is reasonably possible to obtain in colored reproductions of this type. Colors in the photograph may differ slightly from the color values cited in the detailed botanical description which accurately describe the colors of the new *Anthurium*. The photograph comprises a side perspective view of a typical plant of 'Red Sensation' grown in a container.

DETAILED BOTANICAL DESCRIPTION

The cultivar Red Sensation has not been observed under all possible environmental conditions. The phenotype may vary somewhat with variations in environment such as temperature and light intensity without, however, any variance in genotype.

The following observations and measurements describe plants of the new *Anthurium* that were grown in containers in Apopka, Fla., in a polypropylene-covered shadehouse with light levels about 2,500 foot-candles. During the production of the plants, temperatures ranged from 15° C. to 40° C. Plants used for the photograph and description were about one year from planting. Color references are made to The Royal Horticultural Society Colour Chart, 1995 Edition, except where general terms of ordinary dictionary significance are used.

Botanical classification: *Anthurium hybrida* cultivar Red Sensation.

Parentage:

*Female, or seed, parent.*—*Anthurium andreanum* cultivar Chilli Red, not patented.

*Male, or pollen, parent.*—*Anthurium hybrida* cultivar Lady Jane, not patented.

Propagation:

*Type.*—By cuttings.

*Time to initiate roots, summer.*—About 15 to 18 days at 25° C. to 38° C.

*Time to initiate roots, winter.*—About 25 to 30 days at 18° C. to 25° C.

*Time to produce a rooted plant.*—About 30 to 40 days at 18° C. to 38° C.

*Root description.*—Thick, fibrous, fleshy; off-white in color.

*Rooting habit.*—Freely-branching; dense.

Plant description:

*Plant shape.*—Upright and outwardly spreading plant habit; inverted triangle; symmetrical.

*Growth habit.*—Freely clumping, bushy and dense growth habit; about five clumps per plant; moderately vigorous.

*Plant height, from soil level to top of leaf plane.*—About 45 cm.

*Plant height, from soil level to top of inflorescences.*—About 51 cm.

*Plant diameter or spread.*—About 66 cm.

*Foliage description.*—Arrangement: Alternate; simple. Length: About 20.5 cm. Width: About 13.5 cm. Shape: Cordate. Apex: Apiculate; recurving. Base: Cordate. Margin: Entire. Texture, upper and lower surfaces: Leathery; glabrous, smooth. Luster, upper and lower surfaces: Glossy. Venation pattern: Pinnate. Color: Developing and fully expanded leaves, upper surface: Close to 147A. Developing and fully expanded leaves, lower surface: Darker green than 144A. Venation, upper surface: Midvein, close to 144A; lateral veins, close to 147A. Venation, lower surface: Midvein, close to 144A to 144B; lateral veins, close to 144A. Petiole: Length: About 36 cm. Diameter, just below geniculum: About 3 mm. Diameter, at plant base: About 1.1 cm. Texture, upper and lower surfaces: Smooth, glabrous; slightly glossy. Color, upper and lower surfaces: 144A. Geniculum length: About 3.6 cm. Geniculum diameter: About 6 mm. Geniculum texture: Smooth, glabrous; slightly glossy. Geniculum color, upper surface: Close to 144A; with development, tinged with close to 187A. Geniculum color, lower surface: Close to 144A. Wing length: About 5.5 cm. Wing diameter: About 6 mm. Wing color: Close to 144A.

Inflorescence description:

*Inflorescence arrangement.*—Spathes with spadices held above and beyond the foliage. Flowering structures arise from leaf axils. Freely and continuous flowering year-round in India. Typically about five to seven inflorescences per plant. Inflorescences not fragrant.

*Inflorescence longevity.*—Inflorescences last about two months under winter conditions and about three months under summer conditions; inflorescences persistent.

*Spathe.*—Length: About 8 cm. Width: About 6.2 cm. Shape: Cordate. Apex: Apiculate. Base: Cordate. Margin: Entire. Texture, upper and lower surfaces: Leathery; glabrous, smooth; waxy. Luster, upper and lower surfaces: Glossy. Aspect: Reflexed along the midrib. Color: When developing, front and rear surfaces: Close to 45A. Fully developed, front and rear surfaces: Close to 45A.

*Spadix.*—Length: About 4.2 cm. Diameter, at apex: About 4 mm. Diameter, at base: About 6 mm. Shape: Columnar, strongly tapering towards the apex; apex, obtuse; base, obtuse. Cross section: Rounded. Aspect: About 60° from vertical. Color: Immature: 4D. Mature: Close to 46A; color eventually becoming closer to 144A with development.

*Flowers.*—Quantity per spadix: Numerous, about 250. Shape: Rounded. Height: Less than 0.5 mm. Diameter: About 2 mm.

*Reproductive organs.*—Androecium: Anther color: No anthers visible. Gynoecium: Stigma shape: Ovoid. Stigma color: Close to 45B. Ovary color: Close to 45B.

*Scape.*—Length: About 38.5 cm. Diameter: About 5 mm. Strength: Strong. Aspect: Erect to slightly outwardly slanted to about 20° from vertical. Color: Towards the base, 144A; towards the apex, faintly overlain with close to 187A.

*Seed and fruit.*—Seed and fruit development has not been observed on plants of the new *Anthurium*.

Disease/pest resistance: Under commercial production conditions, plants of the new *Anthurium* have not been observed to be resistant to pathogens or pests common to *Anthurium*.

Temperature tolerance: Plants of the new *Anthurium* have been observed to tolerate temperatures from about 15° C. to about to 40° C.

It is claimed:

1. A new and distinct cultivar of *Anthurium* plant named 'Red Sensation', as illustrated and described.

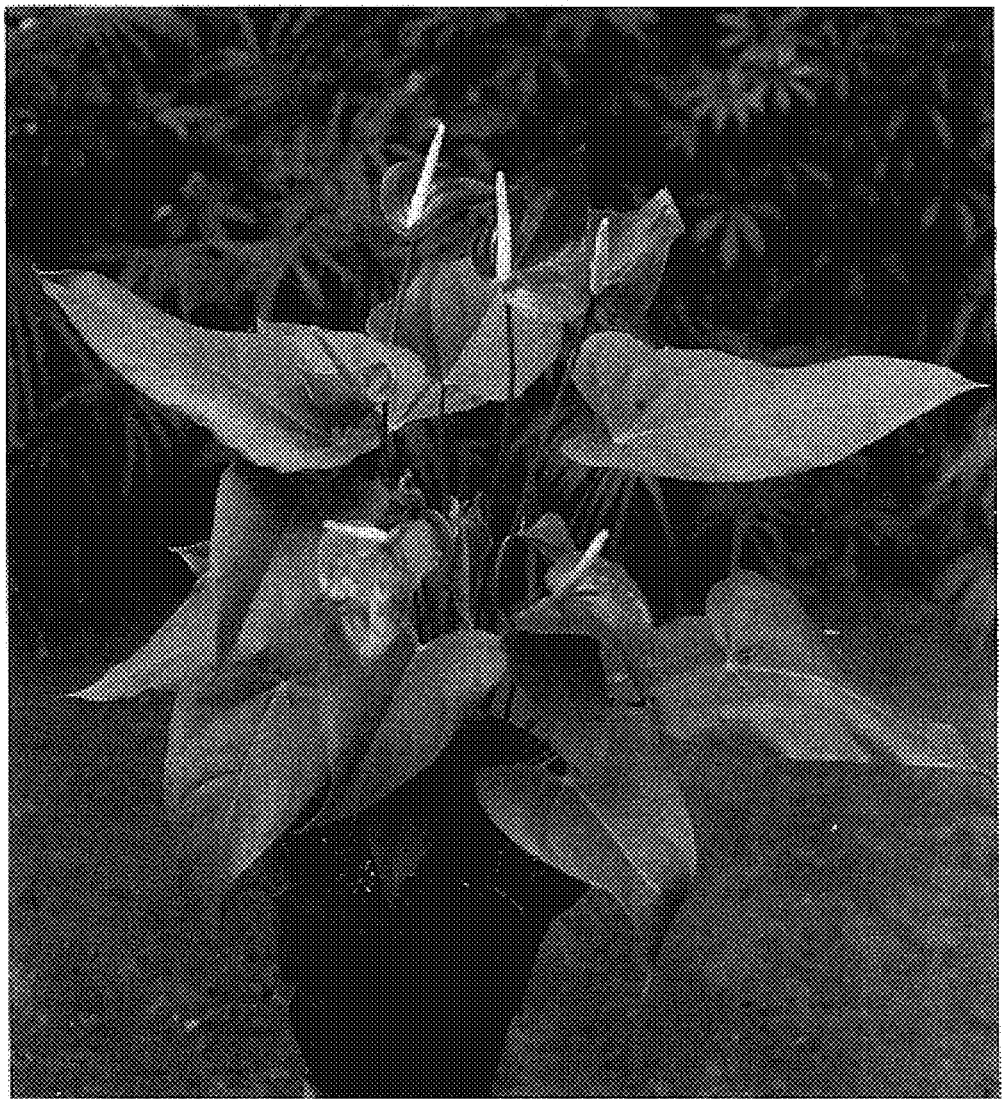

* * * * *